(12) United States Patent
Pein

(10) Patent No.: US 7,905,895 B2
(45) Date of Patent: Mar. 15, 2011

(54) SURGICAL DEVICE FOR REMOVING TISSUE CELLS FROM A BIOLOGICAL STRUCTURE ESPECIALLY FOR LIPOSUCTION

(75) Inventor: Andreas Pein, Einhaus (DE)

(73) Assignee: Human Med AG, Schwerin (DE)

( * ) Notice: Subject to any disclaimer, the term of this patent is extended or adjusted under 35 U.S.C. 154(b) by 1476 days.

(21) Appl. No.: 10/523,294

(22) PCT Filed: Jul. 10, 2003

(86) PCT No.: PCT/DE03/02321
§ 371 (c)(1),
(2), (4) Date: Dec. 28, 2005

(87) PCT Pub. No.: WO2004/014460
PCT Pub. Date: Feb. 19, 2004

(65) Prior Publication Data
US 2006/0111663 A1   May 25, 2006

(30) Foreign Application Priority Data

Jul. 12, 2002 (DE) .............................. 202 11 555 U

(51) Int. Cl.
*A61B 17/32* (2006.01)
*A61N 1/30* (2006.01)

(52) U.S. Cl. ........................ 606/170; 606/167; 604/19

(58) Field of Classification Search .................. 606/167, 606/170; 600/563, 565; 604/19
See application file for complete search history.

(56) References Cited

U.S. PATENT DOCUMENTS

| 4,941,872 | A | 7/1990 | Felix et al. |
|---|---|---|---|
| 5,135,482 | A | 8/1992 | Neracher |
| 5,254,106 | A | 10/1993 | Feaster |
| 5,336,170 | A | 8/1994 | Salerno |
| 5,766,194 | A | 6/1998 | Smith |
| 5,807,313 | A | 9/1998 | Delk et al. |
| 5,968,008 | A | 10/1999 | Grams |
| 2003/0167053 | A1 | 9/2003 | Taufig |

FOREIGN PATENT DOCUMENTS

| DE | 100 33 278 A 1 | 1/2002 |
|---|---|---|
| EP | 0 331 313 | 9/1989 |
| EP | 657 150 | 6/1995 |
| WO | WO 98/06446 | 2/1998 |
| WO | WO 99/22656 | 5/1999 |
| WO | WO0191827 | 12/2001 |

*Primary Examiner* — (Jackie) Tan-Uyen T Ho
*Assistant Examiner* — Melissa Ryckman
(74) *Attorney, Agent, or Firm* — Norris McLaughlin & Marcus, PA; Christa Hildebrand, Esq.

(57) ABSTRACT

In order to reduce the required separating and suction forces on the operational handpiece (1), the slit of the nozzle (8) is inclined at an angle (A) in relation to the plane of the axis of the injection cannula (5) and the angle (A) is selected in such a way that a flat liquid jet (9) is formed with at least one separation tip (10) and a first separation edge(11), in addition to a second separator edge (12), and a separator surface (13).

6 Claims, 6 Drawing Sheets

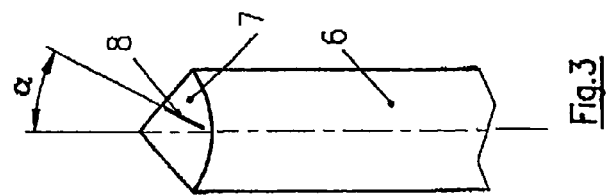
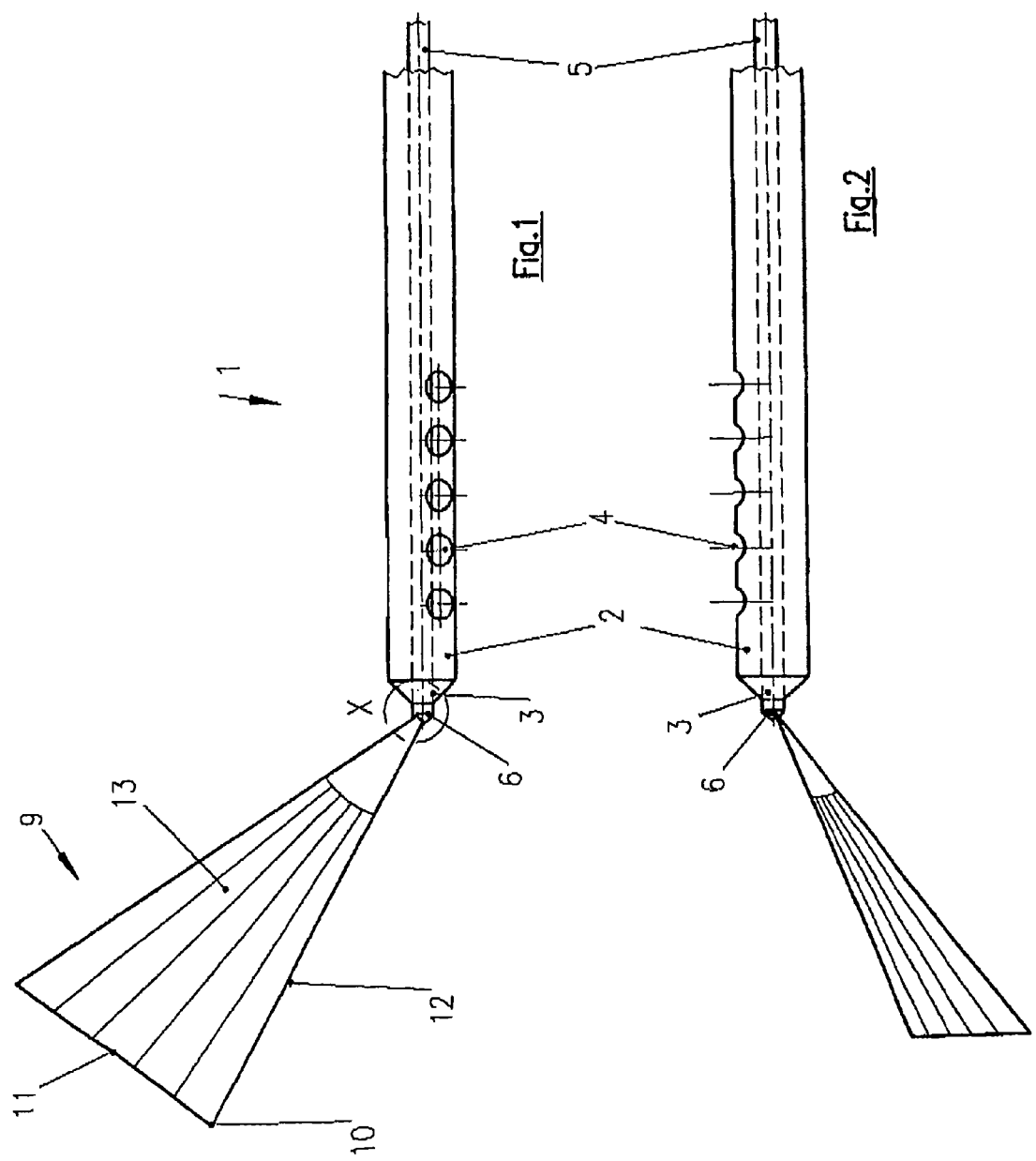

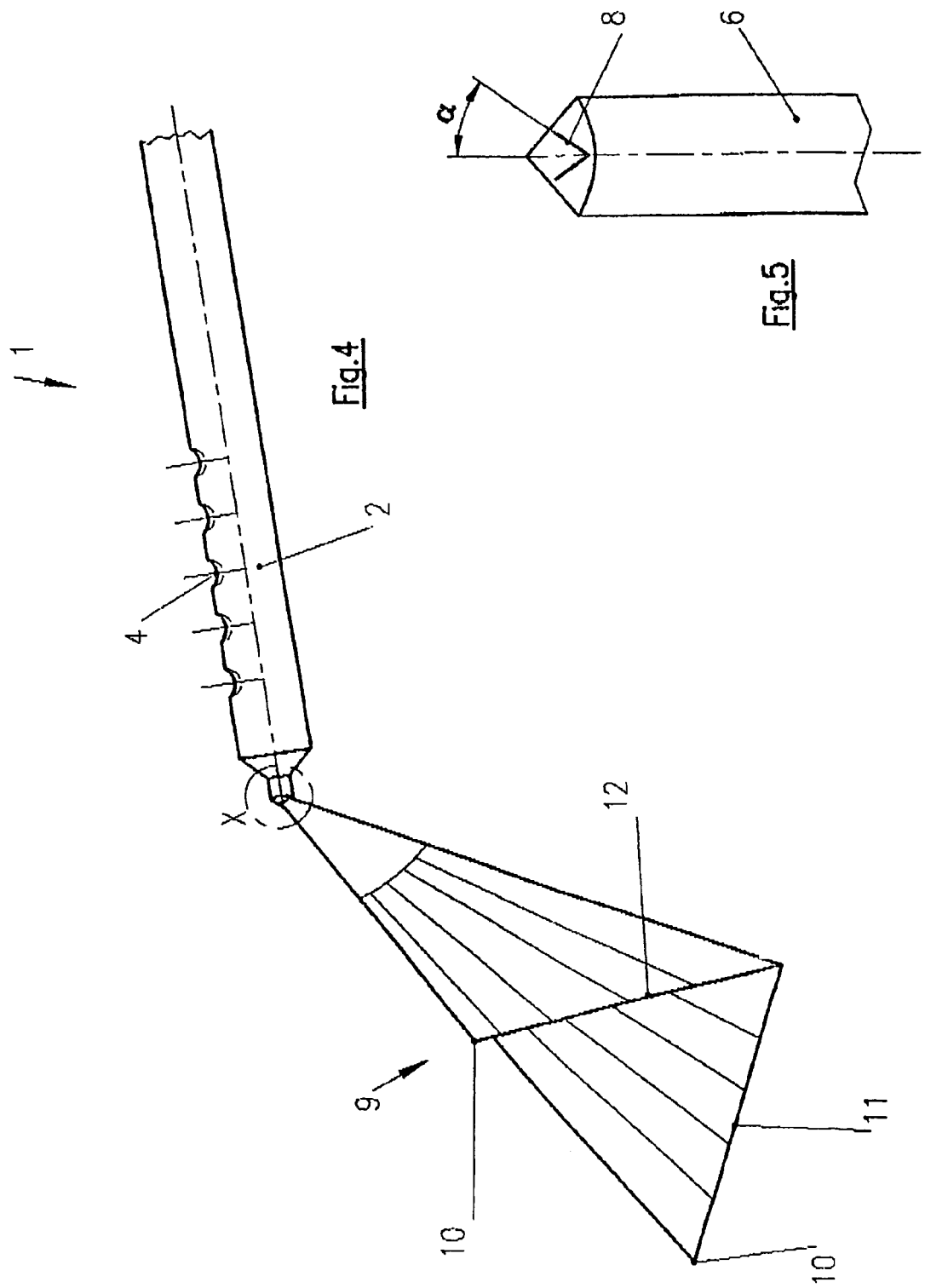

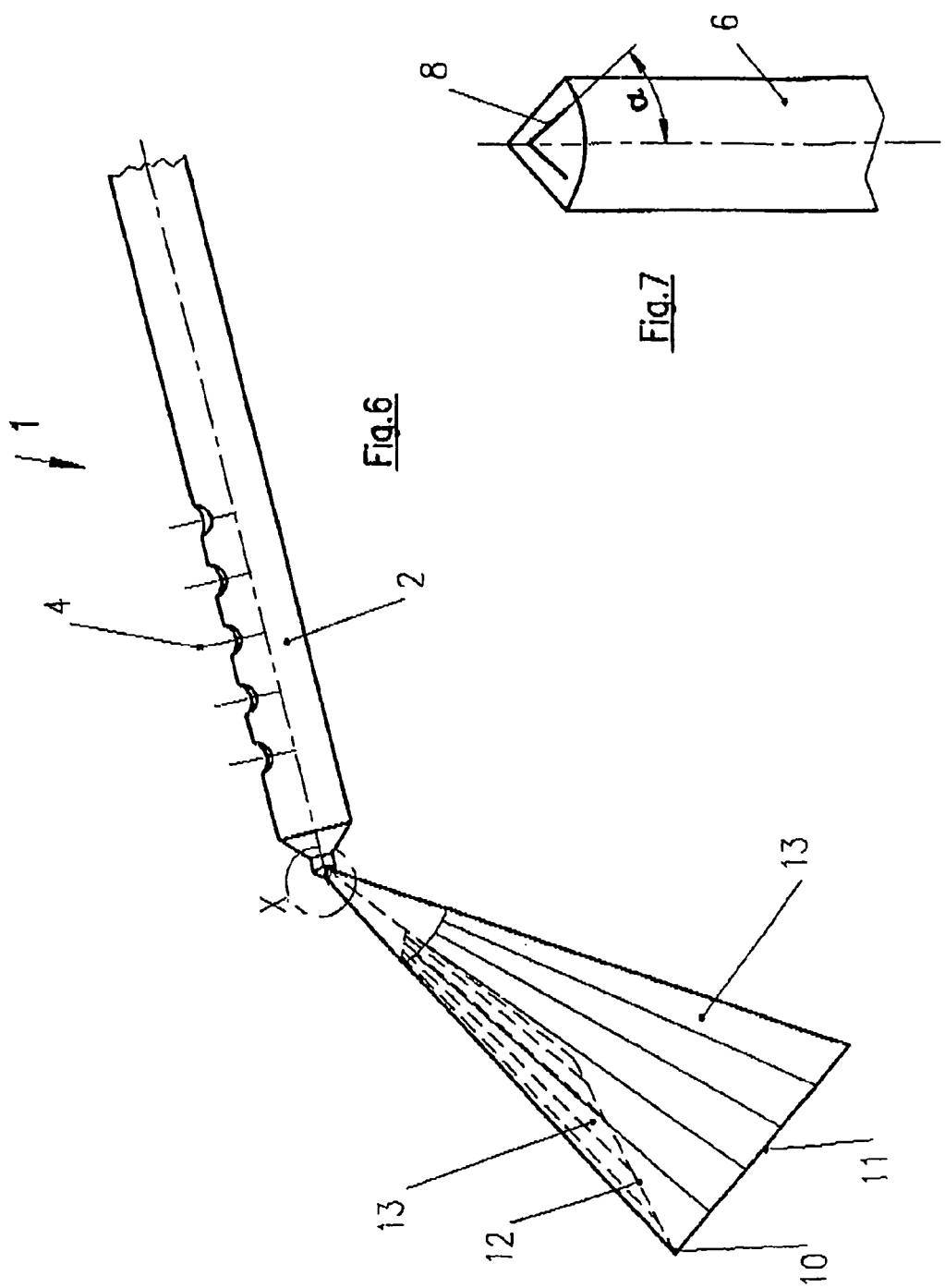

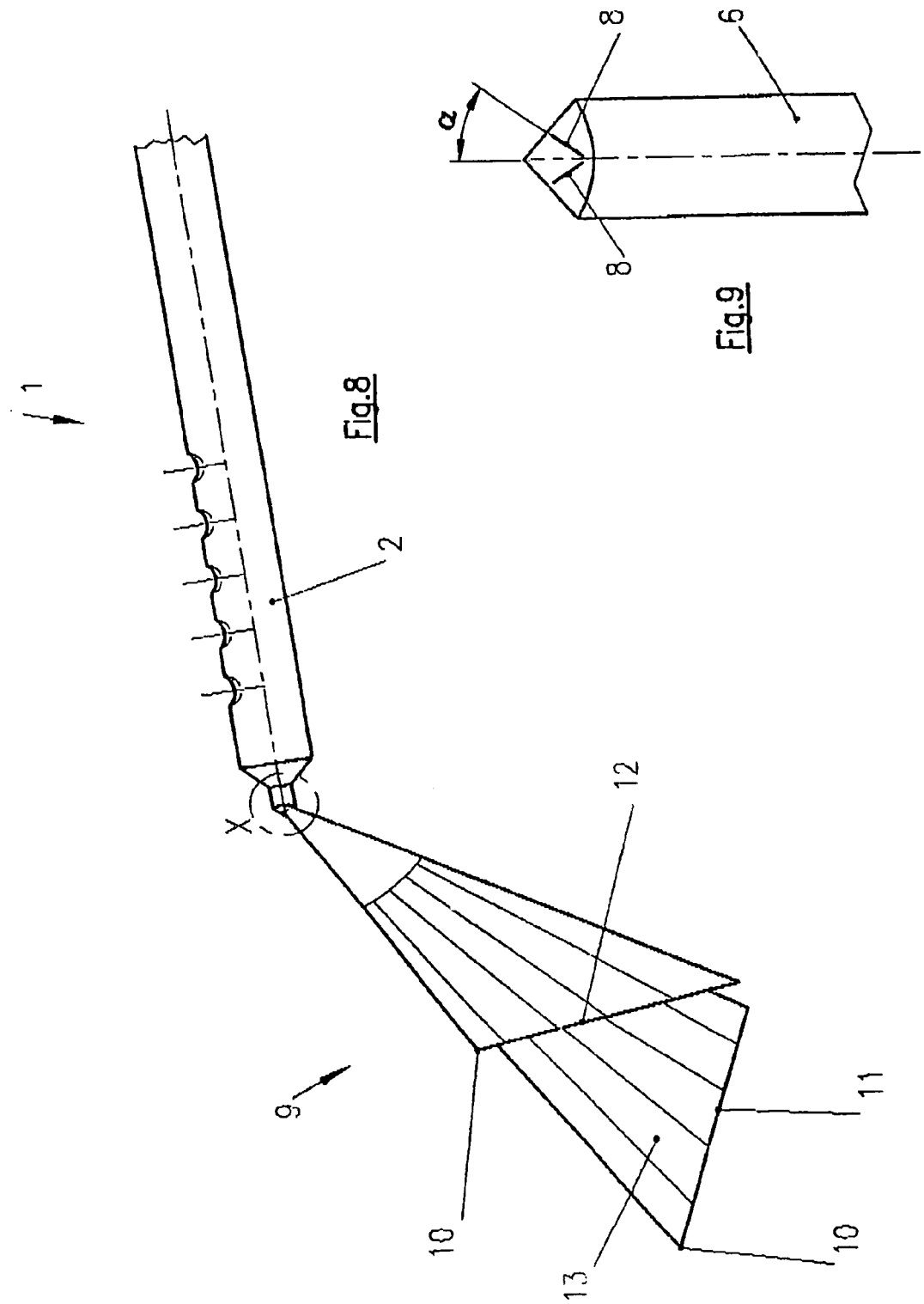

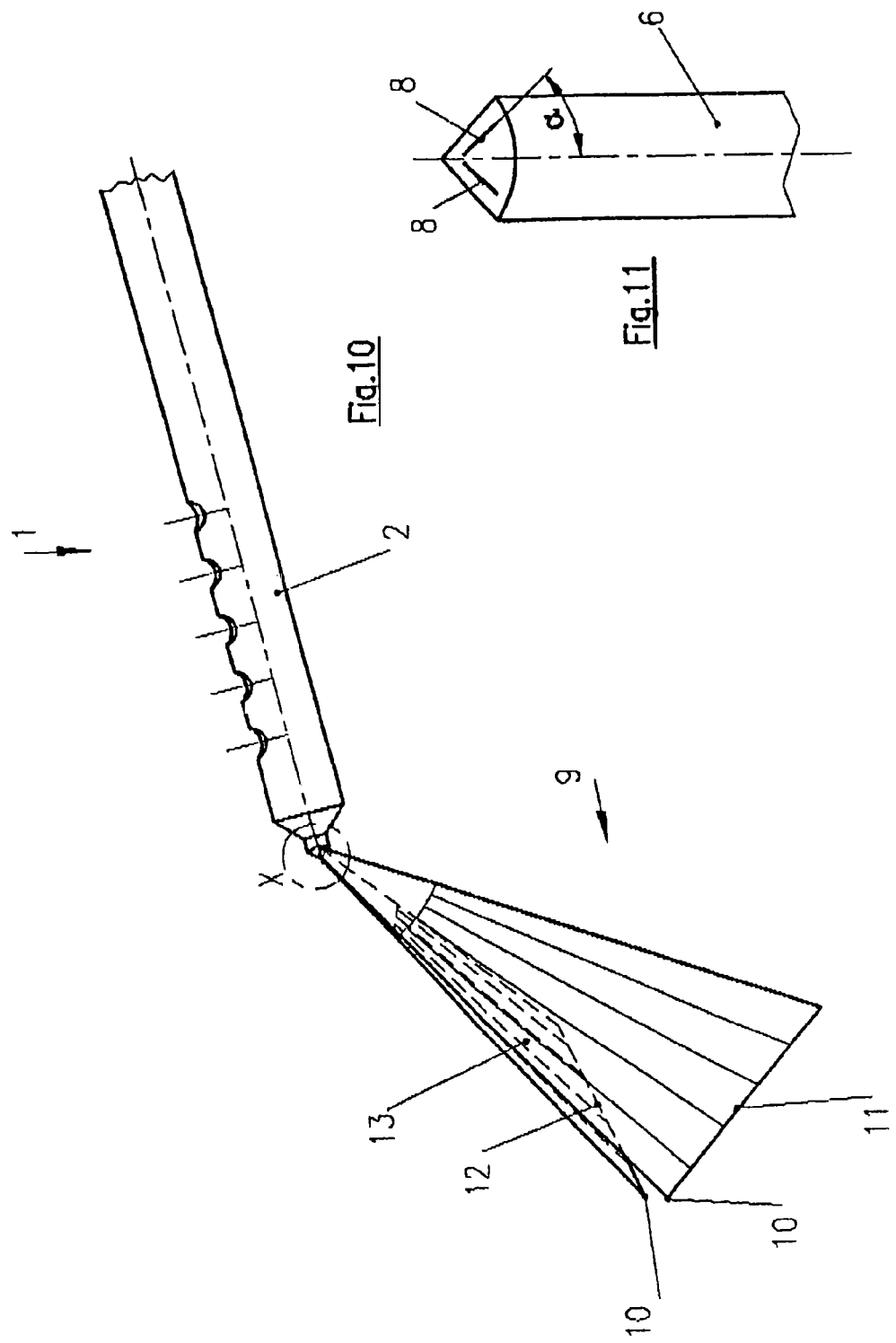

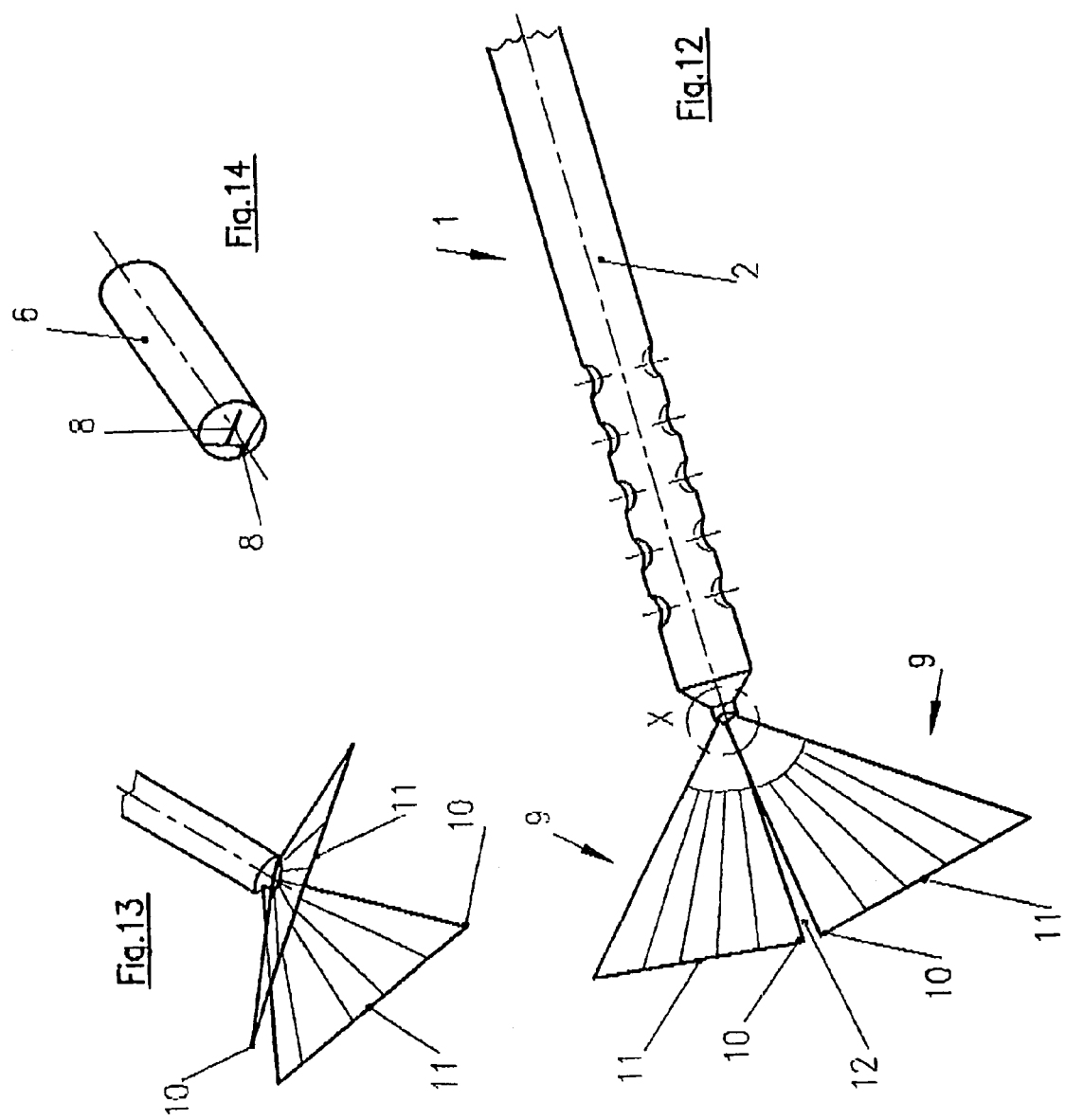

SURGICAL DEVICE FOR REMOVING TISSUE CELLS FROM A BIOLOGICAL STRUCTURE ESPECIALLY FOR LIPOSUCTION

This application is an application filed under 35 U.S.C. 371 of PCT/DE 03/02321, filed Jul. 10, 2003 claiming priority DE 202 11555.0 filed on Jul. 12, 2002.

BACKGROUND OF THE INVENTION

1) Field of the Invention

The invention is directed to a surgical device for removing tissue cells from a biological structure. The device includes a fluid jet device for generating a fluid jet capable of separation and a suction device for suctioning off separated tissue cells and the injected fluid, as well as an operating handpiece connected with the fluid jet device and the suction device. The operating handpiece includes an outer suction tube and an inner injection cannula extending through the suction tube, the outer suction tube and the inner injection cannula form therebetween an annular suction channel. The suction tube includes one or more rows of radial suction openings. The distal end of the injection cannula is closed by a conical tip and the surface of the conical tip includes a nozzle slit that forms a flat jet.

Such devices are used in surgical hospitals for cosmetic purposes and for treating illnesses, as well as for harvesting tissue cells that can reproduce.

2) Description of the Related Art

It is generally known to suction off, for example, excess fatty tissue cells for cosmetic purposes. In a first step, a pressurized working fluid is injected into the fatty tissue, dissolving the fatty tissue in the working fluid by a chemical reaction. In a second step, a suction cannula having a reduced pressure is pushed into the corresponding fatty tissue, whereby the suction force tears the fatty tissue completely out of the connective tissue and removes the mixture of dissolved fatty tissue and working fluid. The mixture is then collected in a receiving container and subsequently disposed of. The suction cannula is formed so as to have several suction openings that are uniformly distributed about its periphery.

U.S. Pat. No. 5,968,008 discloses a suction device for fatty tissue of this type which includes an injection line arranged inside the suction cannula. The injection line terminates in an outlet opening, from which a circular liquid jet exits. With his device, the two separate steps of injecting working fluid and suctioning off fatty tissue using the working fluid are now performed simultaneously, so that the surgical procedure can be performed in less time and continuously. DE 200 09 786 U1 describes a similar suction device for fatty tissue with an injection line having a slit-like exit opening, from which the jet of the working fluid exits in a fan-like shape. This fan-shaped fluid jet supposedly improves the distribution of the working fluid, so that a larger volume of fatty tissue can be uniformly removed.

All the aforedescribed suction devices for fatty tissue are designed to tear the fatty tissue out of the connected tissue through the combined effect of the dissolving power of the working fluid and the force of the suction flow. However, the combined effect from these two components causes problems, because the suction force has a constant value, whereas the dissolution process by the working fluid is time-dependent. Because suction force and dissolving power are not coordinated with each other, the constant suction force is too small at the beginning of the time-dependent dissolution process, as not enough tissue cells have been dissolved, and is too large at the end of the dissolution process, because the tissue cells have all been exposed at the end of the dissolution process. Consequently, the time during which the tissue cells are exposed to the working fluid is either too long or the tissue cells are exposed to an excessively large suction force. In both situations, the tissue cells to be suctioned off as well as tissue cells that should be preserved are destroyed. The human body is subjected to stress which complicates and prolongs the healing process.

The suctioned-off fatty tissue cells are destroyed by the suction process and by the detrimental influence of the working fluid and can then no longer be used.

DE 100 33 278 A1 of the Applicant describes for the first time a device for removing tissue cells from a biological structure. The device is primarily intended to completely separate the excess fatty tissue cells from the adjacent tissue cells by a pressurized fluid jet. The exit opening of the injection line is shaped to form a flat jet is with a frontal cutting edge that operates like a scraping device and therefore effectively peels the fatty tissue cells off. The fluid is pressurized and chemically neutral; the pressurized fluid enters in an intelligent manner between neighboring smooth and soft fatty tissue cells, urges the tissue cells apart, and thereby mechanically separates the strong tendons that hold the tissue together without destroying the tissue cells. The carefully separated tissue cells together with the neutral fluid are suctioned off by a relatively small suction force and are discharged, or alternatively, are separated again from the neutral fluid and reused. This type of surgical devices advantageously separates the fatty tissue cells solely by applying the force of the separation jet, whereas the fatty tissue cells are suctioned off together with the neutral fluid by the force of the suction flow. Unlike with prior art devices, the separation force and the suction force need not be matched and can be selected independent of each other, with the respective forces adjusted to provide the least harmful treatment for the patient. Unlike prior art devices, which produce a fluid intermixed with blood, the novel surgical tissue removal device produces a milky, white suction flow dominated by fatty tissue cells.

However, even this surgical removal device still causes stress in the human body and damage to a large percentage of fatty tissue cells.

It is the therefore an object of the invention to minimize the required separation force and the required suction force of a surgical device of this type.

BRIEF SUMMARY OR THE INVENTION

This object is solved by utilizing a nozzle slit, inclined by an angle ($\alpha$) with respect to the axial plane of the injection cannula, with the angle ($\alpha$) being selected so that a flat fluid jet with at least one separation tip and, on one hand, a first separation edge and, on the other hand, a second separation edge, as well and a peeling surface is formed. More particularly, the novel surgical device is designed to operate with a very small separation force and with a very small suction force. This is particularly easy on the human body during a surgical procedure, but also causes less damage to the tissue cells, which can then be reused for other purposes.

One explanation for the very small separation force is that one does no longer operate with a frontal separation edge, which encounters a significant resistance due to its width and therefore has to apply a large force. Instead, with the novel device, the separation tip initially enters the space between the tissue cells followed by the inclined separation edges, so that the tissue sections to be separated are no longer loosened by a beating motion, but are instead cut off along the separation edge. This pure cutting process encounters a very low resistance, so that the cutting or separation force can be kept small. Advantageously, the required cutting force can be selected by selecting the angle α, i.e., the cutting angle of the separation edge.

The required suction force can also be kept very small, which is easy to explain as follows. Because the separation edge is generally disposed before the suction openings and because the separation forces are oriented in the flow direction, i.e., away from the suction openings, all tissue parts that are exposed to the separation forces also tend to move away from the suction openings. Before the tissue parts that move away can be suctioned off, they must first be slowed down, their direction must be reversed, and they must be accelerated again. As a result, the suction force has to overcome both the separation forces and the inertia of the tissue parts, which represents a complex movement inside the human body. Because of the novel surgical device requires a smaller separation force due to its novel orientation of the flat fluid jet, the recovery process of the tissue parts also requires a smaller force.

Advantageously, the nozzle slit in the novel surgical device can be V-shaped due to the required small separation and suction forces, so that very wide separation edges can be formed, which increase the effectiveness of the surgical device. Advantageously, more than one separated flat fluid jet can be used, which also effectively increases the operating field.

Those skilled in the art will realize that additional embodiments can be selected without departing from the scope of the present invention.

BRIEF DESCRIPTION OF THE DRAWINGS

The invention will now be described with reference to several embodiments.

It is shown in:

FIG. 1 in a first view, the operating handpiece with a flat jet that is inclined twice with respect to the axis, FIG. 2 the operating handpiece of FIG. 1 in another view, FIG. 3 the detail X of FIGS. 1 and 2, FIG. 4 a view of the operating handpiece with a flat jet that is inclined once with respect to the axis, FIG. 5 the detail X of FIG. 4, FIG. 6 the operating handpiece of FIG. 5 with an orientation rotated by 180°, FIG. 7 the detail X of FIG. 6, FIG. 8 the operating handpiece with two flat jets that are inclined with respect to the axis and angled with respect to each other, FIG. 9 the detail X of FIG. 8, FIG. 10 the operating handpiece of FIG. 8 with an orientation rotated by 180°, FIG. 11 the detail X of FIG. 10, FIG. 12 a view of the operating handpiece with two flat jets that are inclined twice with respect to the axis and arranged with respect to each other in form of an impeller, FIG. 13 a different view of the impeller, and FIG. 14 the detail X of FIG. 12.

DETAILED DESCRIPTION OF THE INVENTION

The surgical device for removing vital tissue cells from a biological structure includes a fluid separation device for the separating a biological structure, as described for example in EP 0 551 920 B1 of the same Applicant, and a suction device. Both the fluid separation device and the suction device are generally known and are therefore not illustrated herein. The fluid separation device has a supply container, a pressure pump, and an injection line, whereas the suction device has a collection container, a suction pump, and a suction line. The injection line of the fluid separation device and the suction line of the suction device both terminate in an operating handpiece 1.

The figures in this application show the distal end of the operating handpiece 1. The distal end of the operating handpiece 1 includes an outer suction tube 2, whereby the proximal side of the suction tube 2 is connected with the suction pump of the suction device, and the distal end of the suction tube 2 includes a cone-shaped projection 3 with a center receiving bore. The suction tube 2 includes one or more rows of radial suction openings 4 arranged around the periphery of the suction tube 2 in a particular pattern.

An injection cannula 5 is disposed inside the suction tube 2 and connected on the proximal side by an injection line with the pressure pump of the fluid separation device. The injection cannula 5 is fitted with clearance into the center receiving bore of the suction tube 2, whereby the injection cannula 5 protrudes lengthwise by a certain distance from the through-bore of the suction tube 2. The distal end of the injection cannula 5 is formed as an injection nozzle 6 and accordingly has a conical tip 7 with an apex angle of approximately 90°. One or more nozzle slits 8 with a particular shape and arrangement are disposed in the conical surface of the conical tip 7.

The various figures depict different embodiments of these particular nozzles slits 8 of the injection nozzle 6 and different arrangements of the suction openings 4 in the suction tube 2.

FIGS. 1 to 3 show a nozzle slit 8 that is inclined by an angle α of maximal 300 with respect to the axial cross-sectional plane of the conical tip 7 and which extends from the edge of the cone diameter to the visible edge of the conical tip 7. This results in a flat fluid jet 9 which is twice inclined with respect to the conical axis and thereby forms a forward separation tip 10 with a first separation edge 11 and a second separation edge 12. Both separation edges 11 and 12 are arranged adjacent to the separation tip 10. Also formed is an upper peeling surface 13, on which the separated tissue parts slide off so as to be carried away towards the suction openings 4 in the suction tube 2. The suction openings 4 in the suction tube 2 are hereby arranged in a single row in an axial direction of the suction tube 2 and oriented toward the side of the peeling surface 13 and the location of the separation tip 10.

FIGS. 4 and 5 show a V-shaped nozzle slit 8 having to two branches that extend from a common tip located on the cone edge of the conical tip 7 to the visible edge of the cone tip 7. The two branches of the V-shaped nozzle slit 8 subtend an angle of approximately 90°. This forms an angled fluid jet 9 with two frontal separation tips 10 and a first separation edge 11 and a second separation edge 12.

The peeling surface 13 is enclosed by the angle of the separation jet 9.

FIGS. 6 and 7 show another, likewise V-shaped, angled nozzle slit 8 which is mirror-symmetric to the V-shaped nozzle slit 8 depicted in FIGS. 4 and 5 and forms two outside peeling surfaces 13.

Another embodiment is shown in FIGS. 8 and 9, and FIGS. 10 and 11, respectively. In this embodiment, two V-shaped nozzle slits 8 are arranged with a spacing therebetween. In the embodiment of FIGS. 8, 9, two separation tips 10, a first separation edge 11, a second separation edge 12, as well as two inside peeling surfaces 13 are formed. Two outside peeling surfaces 13 are formed on the fluid jet as a result of the different orientation of the two nozzle slits 8 of FIGS. 10, 11.

Another advantageous embodiment is shown in FIGS. 12 to 14. Two separate nozzle jets 8 are located on either side of the conical tip 7, forming divergent fluid jets 9, which together have the shape of an impeller. A forward separation tip 10, a first separation edge 11 and a second separation edge 12 as well as a peeling surface 13 are associated with each fluid jet 9. The suction tube 2 includes two rows of suction openings 4, wherein each of the row of suction openings 4 cooperates with the peeling surface 13 of a corresponding fluid jet 9.

LIST OF A REFERENCE CHARACTERS

1 operating handpiece
2 suction tube
3 cone-shaped projection
4 suction opening
5 injection cannula
6 injection nozzle
7 conical tip
8 nozzle slit
9 fluid jet
10 separation tip
11 first separation edge
12 second separation edge
13 peeling surface

The invention claimed is:

1. A surgical device for removing tissue cells from a biological structure, comprising
   a fluid jet device for generating a fluid jet capable of separating cells and a suction device for suctioning off separated tissue cells and the injected fluid,
   an operating handpiece connected with the fluid jet device and the suction device,
   wherein the operating handpiece comprises an outer suction tube and a co-axial inner injection cannula extending through the suction tube,
   the outer suction tube and the inner injection cannula forming therebetween an annular suction channel,
   the suction tube includes one or more rows of radial suction openings, and
   the distal end of the co-axial injection cannula is closed by a conical tip having a cone base and forming a surface, the surface includes a nozzle slit that forms a flat jet,
   wherein the nozzle slit is inclined by an angle ($\alpha$) with respect to an axial plane of the injection cannula, with the angle ($\alpha$) being selected so that the flat fluid jet with at least one separation tip, a first separation edge, and a second separation edge and a peeling surface is formed, and wherein
   the angle ($\alpha$) extends from the cone base to one of two visible edges of the conical tip.

2. The surgical device of claim 1,
   wherein the nozzle slit is V-shaped and forms an angled, flat fluid jet.

3. The surgical device of claim 1,
   wherein the angle ($\alpha$) is formed in a direction opposite to the conical tip and the nozzle slit extends parallel to at least one of the two visible edges of the conical tip.

4. The surgical device of claim 3,
   wherein the nozzle slit is V-shaped and forms an angled fluid jet.

5. The surgical device of claim 1,
   wherein at least two separate nozzle jets are arranged on the surface of the conical tip, which produce diverging flat fluid jets, which together assumed the shape of an impeller.

6. The surgical device according to one or more of claims 1,
   wherein the suction tube has as many rows of suction openings as there are peeling surfaces, and each row of suction openings is oriented towards the side of the peeling surface and the location of at least one of the separation tips.

* * * * *